United States Patent
Guidotti et al.

(10) Patent No.: US 7,850,672 B2
(45) Date of Patent: Dec. 14, 2010

(54) ABSORBENT ARTICLE COMPRISING AN ABSORBENT STRUCTURE

(75) Inventors: Ted Guidotti, Göteborg (SE); Gunnar Edwardsson, Bohus Björkö (SE); Malin Eliasson, Mölndal (SE)

(73) Assignee: SCA Hygiene Products AB, Gothenburg (SE)

(*) Notice: Subject to any disclaimer, the term of this patent is extended or adjusted under 35 U.S.C. 154(b) by 243 days.

(21) Appl. No.: 10/809,492

(22) Filed: Mar. 26, 2004

(65) Prior Publication Data

US 2004/0243078 A1 Dec. 2, 2004

Related U.S. Application Data

(60) Provisional application No. 60/457,316, filed on Mar. 26, 2003.

(51) Int. Cl.
*A61F 13/15* (2006.01)
*A61F 13/20* (2006.01)

(52) U.S. Cl. .................. 604/385.101; 604/358; 604/378

(58) Field of Classification Search .......... 604/378, 604/385.201, 385.101
See application file for complete search history.

(56) References Cited

U.S. PATENT DOCUMENTS

| | | | | |
|---|---|---|---|---|
| 5,009,650 | A * | 4/1991 | Bernardin | 604/378 |
| 5,180,622 | A * | 1/1993 | Berg et al. | 428/192 |
| 5,849,003 | A * | 12/1998 | Olsen et al. | 604/387 |
| 6,037,518 | A * | 3/2000 | Guidotti et al. | 604/378 |
| 6,429,351 | B1 * | 8/2002 | Guidotti et al. | 604/378 |
| 6,479,415 | B1 * | 11/2002 | Erspamer et al. | 442/381 |
| 6,613,955 | B1 * | 9/2003 | Lindsay et al. | 604/378 |
| 6,677,498 | B2 * | 1/2004 | Chen et al. | 604/378 |
| 6,869,659 | B2 * | 3/2005 | Shepard et al. | 428/92 |
| 2002/0013563 | A1 * | 1/2002 | Lassen et al. | 604/385.01 |
| 2003/0208175 | A1 * | 11/2003 | Gross et al. | 604/378 |
| 2004/0019340 | A1 * | 1/2004 | McBride | 604/378 |

FOREIGN PATENT DOCUMENTS

| | | |
|---|---|---|
| EP | 0 532 002 B1 | 3/1993 |
| EP | 0 615 736 A1 | 9/1994 |

(Continued)

OTHER PUBLICATIONS

International-Type Search Report (National Application No. 0300878-6).

(Continued)

*Primary Examiner*—Melanie J Hand
(74) *Attorney, Agent, or Firm*—Buchanan Ingersoll & Rooney PC

(57) ABSTRACT

An absorbent article such as a diaper, an incontinence guard, a sanitary napkin or the like, includes a liquid permeable upper surface and an absorbent structure, which in the longitudinal direction exhibits a crotch portion and two end portions, wherein the absorbent structure has an acquisition layer and at least one first storage layer. The first storage layer has at least 50 percent by weight of a super absorbent material calculated on the total weight of the first storage layer. The material of the first storage layer in a dry condition has a density exceeding 0.4 g/cm$^3$. Further, the first storage layer at least in the crotch portion of the absorbent structure has apertures or recesses.

27 Claims, 5 Drawing Sheets

FOREIGN PATENT DOCUMENTS

| | | |
|---|---|---|
| EP | 0 752 892 B1 | 1/1997 |
| JP | 2-61326 | 5/1990 |
| WO | WO 91/11162 A1 | 8/1991 |
| WO | WO 9410956 A1 * | 5/1994 |
| WO | WO 96/20670 A1 | 7/1996 |
| WO | WO 97/34559 A1 | 9/1997 |
| WO | WO 98/00081 A1 | 1/1998 |
| WO | WO 98/26741 A1 | 6/1998 |
| WO | WO 99/63922 A1 | 12/1999 |
| WO | WO 01/21121 A1 | 3/2001 |
| WO | WO 01/21227 A1 | 3/2001 |

OTHER PUBLICATIONS

English Translation of Official Action dated Jun. 2, 2009 in corresponding Japanese Patent Application No. 2006-507914.

* cited by examiner

ABSORBENT ARTICLE COMPRISING AN ABSORBENT STRUCTURE

CROSS-REFERENCE TO RELATED APPLICATIONS

The present application claims the benefit of U.S. Provisional Application No. 60/457,316, filed in the United States on Mar. 26, 2003, the entire contents of which are hereby incorporated herein by reference.

BACKGROUND OF THE APPLICATION

1. Field of the Invention

The present invention relates to an absorbent article such as a diaper, an incontinence guard, a sanitary napkin or the like, whereby the article includes a liquid permeable upper surface and an absorbent structure having an acquisition layer and a storage layer.

2. Background

Absorbent articles such as diapers, incontinence guards, sanitary napkins, intended for one single use, are usually constructed by an absorbent structure having the capability to acquire large amounts of liquid under a short period of time, having further the ability to distribute the liquid and to store the liquid. This means that the absorbent structure usually comprises several different layers having different properties with respect to each other. Frequently, the absorbent structure at least comprises a liquid acquisition layer and a liquid storage layer. The liquid storage layer often comprises a cellulosic fluff pulp layer mixed with super absorbent material, which are polymers having the ability to absorb water or bodily fluids many times their own weight. The liquid acquisition layer often comprises a porous fibrous layer of synthetic fibers.

Upon usage of such absorbent articles it is desirable that they are thin and discreet to wear, and that they at the same time can rapidly acquire large amounts of liquids discharged under a short period of time and store this liquid in the article.

EP 0 532 002 relates to an absorbent structure, mainly for use in diapers and incontinence guards. The absorbent structure contains at least 30 percent by weight of a super absorbent material and the super absorbent material exhibits some ability to distribute liquid and resist compression during load. The purpose of the described absorbent structure is to obtain a thin structure having a sufficient absorption capability.

EP 0 752 892 relates to an absorbent structure, mainly for use in diapers and incontinence guards. The absorbent structure contains at least 60 percent by weight of a super absorbent material and the super absorbent material exhibits certain properties. The purpose of the described absorbent structure is to obtain a thin structure having a sufficient absorption capability.

However, it has still been difficult to obtain sufficient liquid acquiring capacity, liquid distribution capacity and liquid storage capacity, which at the same time are thin and discreet to wear.

SUMMARY

An article is disclosed herein which is thin and discreet to wear, and, at the same time, exhibits sufficient liquid acquiring capacity, liquid distribution capacity and liquid storage capacity.

In the absorbent article, the material of the first storage layer in a dry condition, has a density exceeding 0.4 g/cm$^3$, and the first storage layer includes apertures/recesses at least in the crotch portion of the absorbent structure.

Preferably, the material of the first storage layer in a dry condition is even more compressed and exhibits a density exceeding 0.5 g/cm$^3$. According to a further embodiment, the first storage layer exhibits a density exceeding 0.6 g/cm$^3$ According to an embodiment, the material of the first storage layer comprises at least 60 percent by weight of a super absorbent material, calculated on the total weight of the first storage layer in a dry condition. According to another embodiment, the material of the first storage layer comprises at least 70 percent by weight of a super absorbent material, calculated on the total weight of the first storage layer in a dry condition. The material of the first storage layer may also comprise 90 percent by weight or more of the super absorbent material, calculated on the total weight of the first storage layer in a dry condition. An advantage with such a high content of the super absorbent material is that a very thin and discreet article is obtained. As the content of super absorbent material is high, the amount of the super absorbent material is also relatively high, which in turn leads to a high absorption capacity and a high liquid storing capacity.

According to an embodiment, the apertures/recesses extend through the entire thickness of the first storage layer.

According to an embodiment, the apertures/recesses extend along the longitudinal direction of the absorbent structure. Thus, the apertures/recesses create longitudinal channels in the first storage layer. One advantage with such longitudinal channels is that they direct the liquid transport in a direction towards the end portions of the absorbent structure.

Naturally, it is possible to have other physical designs of the apertures/recesses, for example, the apertures/recesses could be circular or designed in a way that channels are obtained in the transversal direction of the absorbent structure. Using this construction, the first storage layer also functions as a forming element.

According to one embodiment the width of the material between the apertures/recesses, at least in the crotch portion, is maximally 20 mm. A material layer, which firstly comprises super absorbent material at a high content and secondly exhibits a density exceeding 0.4 g/cm$^3$ absorbs relatively slowly. It has also been shown that the liquid transport rate in the planar extension of the storage layer decreases to a large extent after the liquid has been moved about 10 mm. In order to use the total capacity of the entire storage layer, it has thus been shown that the width of the material between the apertures/recesses, at least in the crotch portion, does preferably not exceed 20 mm.

The first storage layer of the absorbent article exhibits a first surface being faced against the liquid permeable surface of the article, and a second surface being faced away from the liquid permeable surface of the article.

According to one embodiment, the acquisition layer lies close to the second surface of the first storage layer, i.e., the surface that in the article is faced away from the user. In the cases where the liquid permeable surface is comprised of a separate liquid permeable top sheet, the liquid permeable top sheet and the acquisition layer are thus arranged on different sides of the first storage layer. The acquisition layer is preferably a porous layer having the capability to rapidly acquire a large amount of liquid. The first storage layer containing a high percentage of super absorbent material has a better ability to retain liquid than does the acquisition layer. Thus, by placing the storage layer between the liquid permeable top sheet and the acquisition layer, the risk is decreased that the surface being closest to the user becomes wet after a first wetting. In order to obtain a sufficient contact between the layers, it has been shown to be advantageous to join the liquid permeable topsheet to the acquisition layer by means of the hollow spaces being obtained by the apertures/recesses in the first storage layer. Preferably, the joining is thermal. Naturally, it is preferable that the thermal joining of the liquid permeable layer and the acquisition layer is sufficient to hold the layers together. However, it has been shown that it is preferable that the joining surface does not occupy an area being too large. Upon welding, a liquid impermeable surface is created and if this surface is allowed to be too large, a risk arises that the liquid inlet ability is decreased. In order to eliminate the risk of liquid leakage and at the same time obtain a sufficient joining of the layers, it has, for instance, been shown to be advantageous to use a welding surface, whose width maximally is 1 mm. According to another way of defining the design of the welding surface, it has been shown to be advantageous to design the welding in such a way that the portion of the welded surface, calculated on the entire surface of the top sheet covering the apertures/recesses does not exceed 50%, more preferably does not exceed 40%, and most preferably does not exceed 20%. The welding can, for example, comprise a plurality of spot welds or weld beads, which are arranged having the same distance to each other or arranged in a particular pattern exhibiting different distances to each other;

According to one embodiment, the acquisition layer lies close to the first surface of the storage layer.

According to one embodiment, the acquisition layer is a super absorbent foam material, for instance a polyacrylate based foam material. A polyacrylate-based foam material is produced by the saturation under pressure using carbon dioxide of a solution, which at least contains monomer, a cross-linking material, an initiator and a tenside in a vessel, during stirring. When the solution is removed from the vessel through a nozzle, the solution is expanded and a foamed structure is achieved. The foamed structure is then locked in that polymerisation and cross-linking are initiated by for instance UV radiation and/or e-beam radiation. Finally, the material is compressed and dried.

An advantage using such a super absorbent foam material is that the material is soft and flexible. Preferably, the foam material exhibits a Gurley stiffness value being lower than 1000 mg. Preferably, the material also exhibits a density in a dry condition exceeding 0.5 g/cm$^3$. Such a super absorbent foam material expands heavily upon contact with water. At the expansion the free volume of the material is increased, such that a super absorbent material can receive a large amount of liquid under a short period of time.

According to another embodiment, the acquisition layer is a fibrous layer including polyacrylate-based particles or a polyacrylate-based coating bonded to the fibrous layer, wherein the polyacrylate-based particles or the polyacrylate-based coating is bonded to the fibrous layer in that acrylic acid monomers are sprayed onto the fibrous layer, whereby the acrylic acid monomer is allowed to polymerize. An example of such a material is a nonwoven material of for instance polyester. Drops of acrylic acid monomers are sprayed onto the nonwoven material, whereby the acrylic acid monomer is allowed to polymerize. The formed polymerised polyacrylic acid particles also function, in addition to as a liquid absorbent material, as a binding agent in that the particles maintain their entire structure in a compressed condition by means of hydrogen bonds between oxygen in the carboxylic groups of the acrylic acid. Upon wetting, the existent hydrogen bonds are broken, whereby the material expands to its uncompressed condition. Thereafter, the material swells further due to the swelling of the super absorbent material upon absorption of liquid. It results in a material being thin and relatively heavily compressed, but when the material thereafter is being wet, the material exhibits a large amount of free volume and high permeability. A further advantage with such an acquisition layer, is that the super absorbent particles bind the liquid not being drained by a storing layer, whereby the risk that the surface being closest to the user becomes wet after a fist wetting, is decreased. The embodiment also covers other ways to bind a super absorbent material to a fibrous structure. In order to further improve such an acquisition layer, it has been shown to be an advantage to corona-treat the acquisition layer. In corona treating, the layer is treated with plasma, which is a gas being subjected to enough energy to entirely or partly ionize the gas. The contact with the energy-rich gas with the surface of the material, results in that radicals are formed on the surface of the material. Thereafter, different types of functional groups are introduced, such as for example, oxygen-containing functional groups. The advantage using such a corona-treated material is that it exhibits an improved liquid distributing ability compared to a non-corona-treated material.

A further preferred property of the absorbent structure, is that the liquid transport ratio between the acquisition layer and the first storage layer is such that the first storage layer drains liquid from the acquisition layer. It has been shown that an acquisition layer exhibiting a good ability to be drained of liquid by the storage layer, is defined such that at least 50% of the pores in the material of the acquisition layer are emptied from liquid at a pressure being lower than 12 cm $H_2O$. The method being used upon measuring the drainage ability is a TRIs porosimeter. The pressure when at least 50% of the pores in the material are emptied is denoted $PV_{50}$ (cm $H_2O$).

According to a further embodiment, the absorbent structure also comprises a second storage layer. The second storage layer preferably contains a lower amount of super absorbent material calculated on the total weight of the second storage layer than the first storage layer. The second storage layer lies for instance close against the liquid permeable back sheet. Further, the second storage layer preferably has a larger extension than the first storage layer in the plane of the article. Thus, the second storage layer functions as an extra security zone, i.e., it absorbs liquid that might be present outside the first storage layer or outside the acquisition layer. It is also possible that the second storage layer entirely or partly encloses the first storage layer. Preferably, the second storage layer is thereby arranged both against the surface of the first storage layer being closest to the user during use of the article, and the surface of the first storage layer which during use of the article is most distantly arranged from the user, i.e., the second storage layer is wrapped around the first storage layer. The hollow spaces in the first storage layer are essentially free from fibers, however, for the described embodiment using a second storage layer being arranged on each side of the first storage layer, it is possible that single fibers from the second storage layer, entirely or partly, extend through the hollow spaces in the first storage layer. The advantage with such a structure is that the single fibers may direct the liquid transport towards the hollow spaces, and thus facilitate the transport of liquid to the first storage layer. Using this kind of design of the absorbent structure, it is possible to have the first storage layer arranged in the crotch portion of the article and the second storage layer to be arranged both in the crotch portion and in the end portions.

DETAILED DESCRIPTION OF THE PREFERRED EMBODIMENTS

Figure 1:
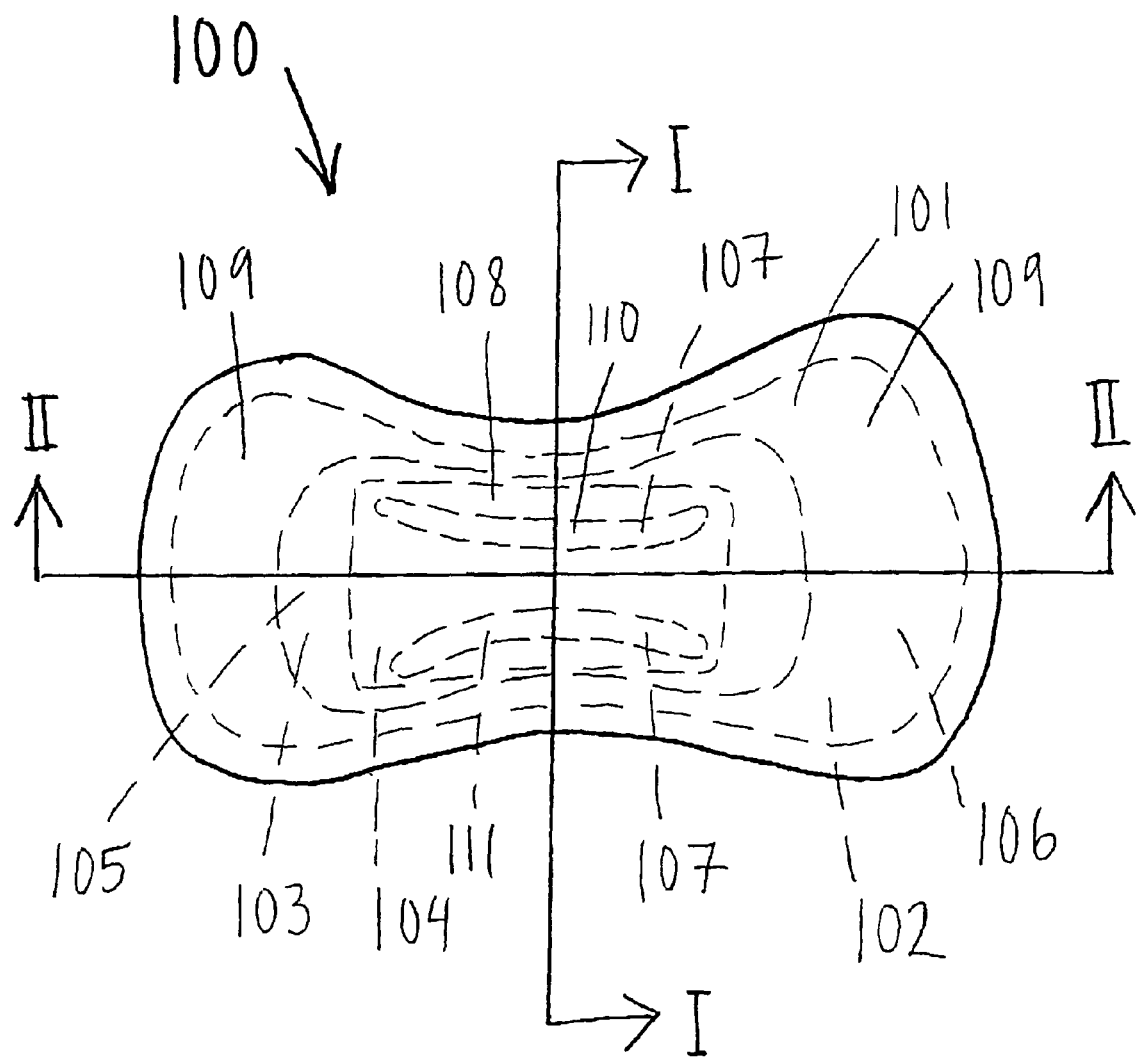
FIG. 1 shows a planar view of an embodiment of an absorbent article according to the invention.

The following description refers to a couple of embodiments of absorbent articles according to the invention, which is thus not limited to the below described embodiments. In FIG. 1 a planar view is shown of an absorbent article 100 according to the invention. The absorbent article 100 exhibits a transverse direction, being shown by a transversally extending center line I, and a longitudinal direction being shown by a longitudinally extending center line II. Further, the absorbent article 100 has a thickness direction, being directed perpendicularly against the plane. The absorbent article 100 has a liquid permeable top sheet 101, which during use of the article is intended to lie close to the user. Further, the absorbent article 100 has a back sheet 102, which is at least substantially liquid impermeable, and an absorbent structure 103 enclosed between the liquid permeable top sheet and the back sheet. The material of the back sheet 102 may optionally be a so called vapor permeable breathable material. The absorbent structure has a crotch portion 108 and two end portions 109. The absorbent structure 103 comprises an acquisition layer 104, which is intended to rapidly be able receive a large amount of liquid and a first storage layer 105, which is intended to rapidly be able store a large amount of liquid, and a second storage layer 106. The first storage layer 105 is arranged closest to the liquid permeable top sheet 101, the second storage layer is arranged closest to the substantially liquid impermeable backsheet 102 and the acquisition layer 104 is arranged between the first storage layer 105 and the second storage layer 106. The second storage layer 106 has a longer extension in the plane of the article than the first storage layer 105, but exhibits a lower total absorption capacity. The second storage layer also functions as a form rendering element in such way that it assists in creating and maintaining an absorbent structure being flexible against the body. The first storage layer 105 exhibits two longitudinally arranged apertures/recesses 110, 111. The hollow spaces obtained through the apertures/recesses 110, 111 extend in the longitudinal direction of the article. The distance between the apertures/recesses 110, 111 is preferably maximally 20 mm in the crotch portion. The distance refers to the length of the material between the apertures/recesses 110, 111 in the transverse direction of the article. Close to the end portions 109, the distance between the apertures/recesses is preferably somewhat longer than in the crotch portion. Such a shape is advantageous since both a narrow crotch portion and a shape adapted to the body is obtained.

It is also possible that the apertures/recesses 110, 111 in the first storage layer 105 have other shapes. For example, it is possible that the apertures/recesses extend in the transverse direction of the article, whereby transversally arranged channels are obtained. An advantage of this design is that such a storage layer may assume a cup shape relatively easy. Another alternative embodiment is circular apertures/recesses. Naturally, other shapes of the apertures/recesses are possible.

The storage layers 105, 106 may comprise optional absorbent materials, such as fibrous materials, foam materials, superabsorbent polymers and combinations thereof. According to one embodiment, the first storage layer 105 is a fibrous structure comprising at least 50 percent by weight of a super absorbent material calculated on the total weight of the first storage layer 105. Super absorbent materials are polymers having the capability to absorb water or bodily fluids many times their own weight. Conventionally super absorbent materials are polymers such as polyacrylic acid. The super absorbent material is in the shape of powder, flakes, fibers, granules or the like. The super absorbent material may be mixed with the fiber material or may be applied in the form of one or more layers between fiber layers. The super absorbent material is either equally distributed in the first storage layer 105 or distributed in various concentrations in the longitudinal and/or the thickness direction of the first storage layer 105. It is also possible to use a substantially pure layer of super absorbent material in the first storage layer. One example of a suitable super absorbent material is a super absorbent material having the ability to rapidly absorb liquid. A super absorbent material, which can absorb 5 grams of bodily fluids per gram super absorbent material in 10 seconds, is usually defined as a fast super absorbent material. An example of a fast liquid-absorbing super absorbent material is a particulate super absorbent material having a small particle size, i.e., a low particle diameter. Such a particulate super absorbent material usually exhibits an average particle size of between 150 µm and 400 µm. It is also possible to use several types of super absorbent material, for example is it possible to use a super absorbent material which absorbs very rapidly in the first storage layer and a conventional super absorbent material absorbing slower in the second storage layer.

Also, the second storage layer 106 can, according to one embodiment, comprise a fibrous structure containing superabsorbent material. The percentage super absorbent material in the second storage layer 106 is preferably lower than the amount of super absorbent material in the first storage layer 105. For example, the second storage layer 106 may comprise about 10 percent per weight of a super absorbent material calculated on the total weight of the second storage layer 106. The second storage layer 106 has a longer extension in the plane of the article, but exhibits a lower total absorption capacity.

The bodily fluids, for example urine, penetrate through the liquid permeable top sheet and is then brought via the hollow spaces, i.e., the apertures/recesses in the first storage layer 105, further to the acquisition layer 104. The acquisition layer 104 is then drained of liquid by the first storage layer 105. The acquisition layer 104 may therefore without difficulties receive a second dose of liquid. The first storage layer 105 has the capacity to store several doses of liquid. Since the first storage layer is heavily compressed, it has been shown difficult for the liquid to penetrate the upper part of the structure. A cellulosic fluff pulp mixed with a high content of super absorbent material, whose structure is highly compressed, exhibits a relatively lustry, glossy upper surface, which is difficult to penetrate for the discharged bodily fluid. By providing the apertures/recesses 110, 111 in the highly compressed material, an access to the inner porous structure is created in the first storage layer 105. This facilitates the liquid absorbing capacity of the first storage layer 105.

The acquisition layer 104 is preferably a super absorbent foam material or a fibrous layer having super absorbent particles or a super absorbent coating bound to the fibrous layer. Naturally, the acquisition layer can also constitute a fibrous layer that does not contain super absorbent material. For example, the acquisition layer may comprise a synthetic fiber layer of, for example, polyethylene, polypropylene, polyester, or copolymers thereof. It is also possible that the synthetic fibers are conjugated fibers.

The liquid permeable top sheet is a non-woven material or an apertured plastic film, or a laminate thereof. Examples of polymers of which the liquid permeable top sheet may be made include polyethylene, polypropylene, polyester, or copolymers thereof. To enable the liquid permeable top sheet 101 to rapidly let the discharged bodily fluid through, the top sheet is often coated with tensides and/or is apertured. Since the first storage layer 105 is highly compressed and exhibits a high density, it is preferable that the discharged liquid rapidly reaches the hollow spaces in the first storage layer 105. Therefore, an open liquid permeable top sheet has been shown to be advantageous. An example of an open material is a layer of continuous tow fibers, which are joined in points, lines or spots, in a bonding pattern but are otherwise substantially not connected to each other.

Figure 2:
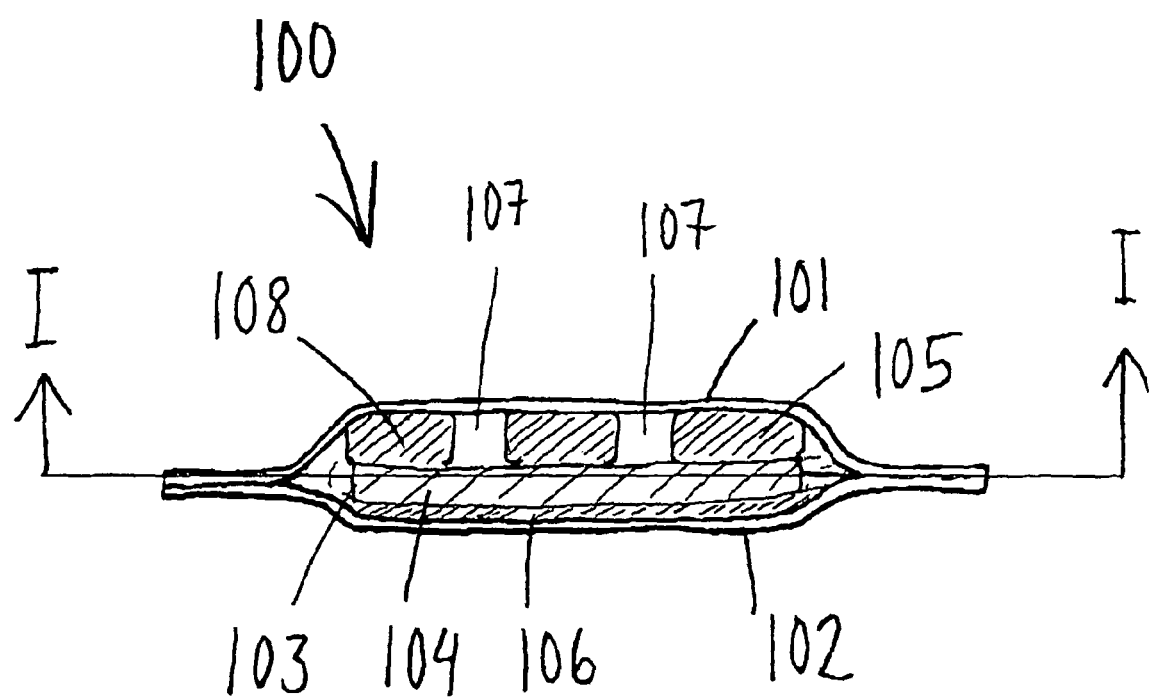
FIG. 2 shows a cross-section of the absorbent article shown in FIG. 1.

FIG. 2 shows a cross-section in the crotch portion 108 of the absorbent article 100 shown in FIG. 1. Thus, the absorbent article 100 has a liquid permeable top sheet 101, which during use of the article is intended to lie closest to the user, a back sheet 102, and an absorbent structure 103 enclosed therebetween. The absorbent structure 103 comprises an acquisition layer 104, which is intended to be able to rapidly receive a large amount of liquid, a first storage layer 105, which is intended to be able to rapidly store a large amount of liquid, and a second storage layer 106 having a longer extension in the plane of the article, but which has a lower total absorption capacity. The first storage layer 105 has two longitudinally arranged apertures/recesses/hollow spaces 107. The distance of the material between the two apertures/recesses is preferably maximally 20 mm in the crotch portion 108. The first storage layer 105 is arranged closest to the liquid permeable top sheet 101, the second storage layer 106 is arranged closest to the substantially liquid impermeable backsheet 102 and the acquisition layer 104 is arranged between the first storage layer 105 and the second storage layer 106.

Figure 5:
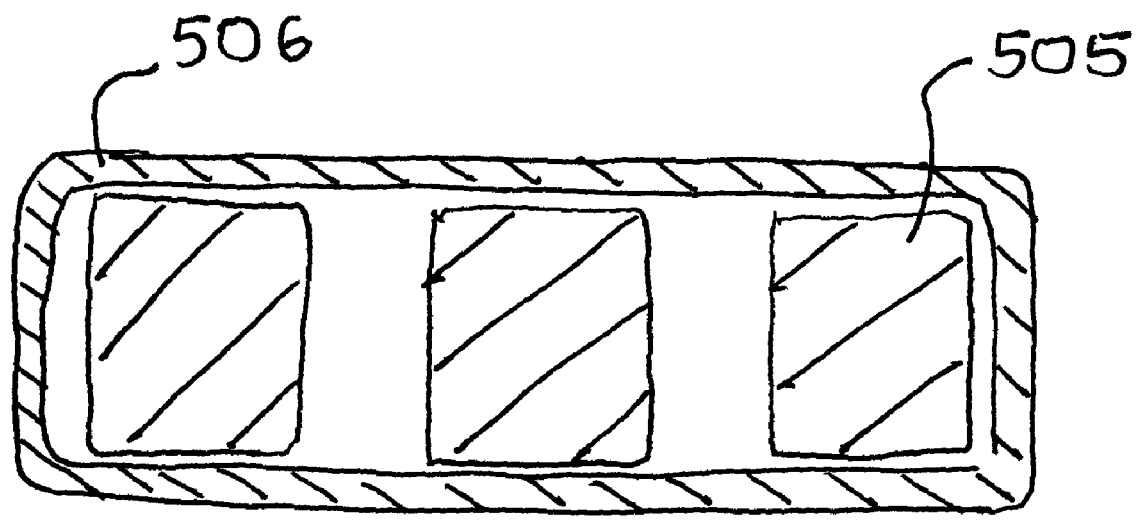
FIG. 5 shows a first storage layer and a second storage layer portion of the embodiment of FIG. 1.

FIG. 5 shows a variation of the embodiment shown in FIG. 1 whereby a second storage layer 506 fully or partially encloses a first storage layer 505. The second storage layer 506 is arranged both against the surface of the first storage layer 505 being closest to the user during use of the article, and the surface of the first storage layer 505 which during use of the article is most distantly arranged from the user.

Figure 3:
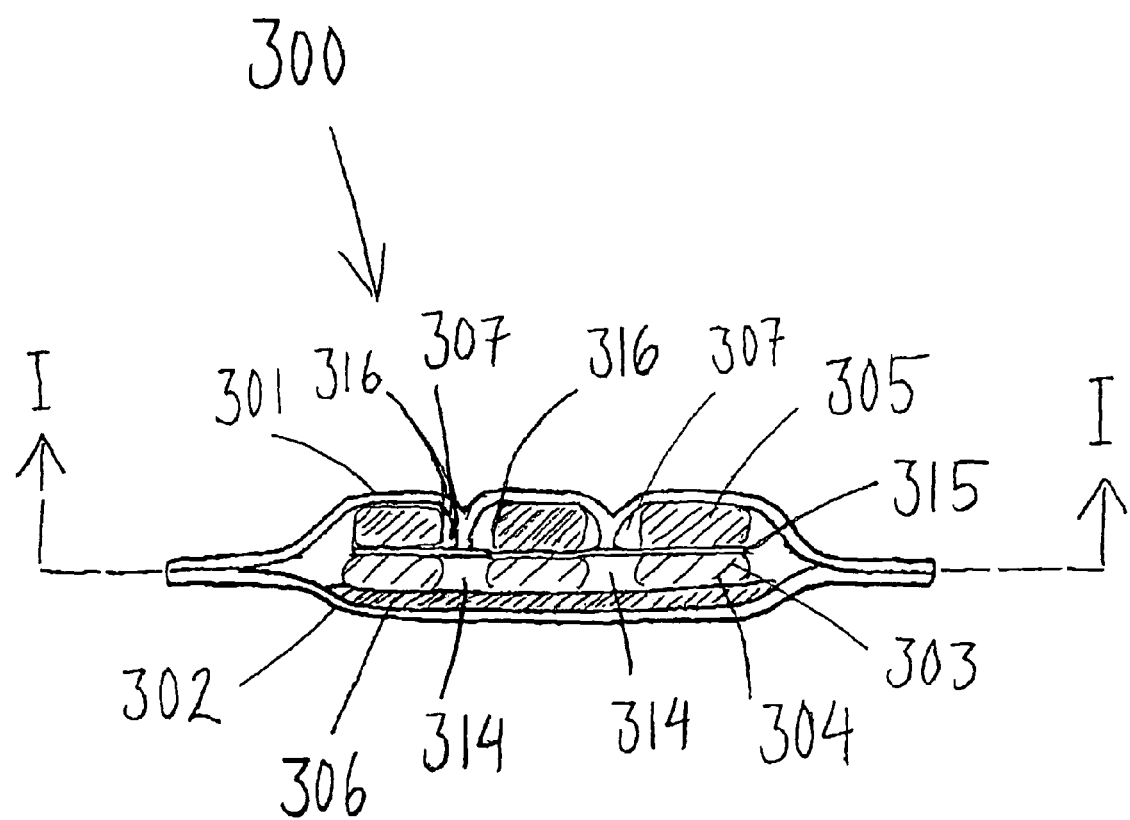
FIG. 3 shows a cross-section of an alternative embodiment of an absorbent article according to the invention.

FIG. 3 shows a cross-section along a transversally extending center line I of an alternative embodiment of an absorbent article 300 according to the invention. The absorbent article 300 has a liquid permeable top sheet 301, which during use of the article 300 is intended to lie closest to the user, a back sheet 302, and an absorbent structure 303 enclosed therebetween. The absorbent structure 303 comprises an acquisition layer 304, which is intended to be able to rapidly receive a large amount of liquid, a first storage layer 305, which is intended to be able to rapidly store a large amount of liquid, and a second storage layer 306 having a longer extension in the plane of the article, but which has a lower total absorption capacity than the first storage layer 305. The first storage layer 306 preferably has a lower grammage than the first storage layer 305. The first storage layer 305 is arranged closest to the liquid permeable top sheet 301. The first storage layer 305 exhibits two longitudinally arranged apertures/recesses 307. The first storage layer 305 is a fiber structure containing at least 50 percent by weight of super absorbent material calculated on the total weight of the first storage layer 305.

The second storage layer 306 preferably comprises cellulosic fibers and super absorbent material. The percentage of super absorbent material in the second storage layer 306 is preferably lower than the percentage super absorbent material in the first storage layer 305. The second storage layer 306 functions as a kind of security zone, i.e., the second storage layer 306 will ensure that liquid that may appear outside the acquisition layer 304 or the first storage layer 305, does not leak out from the absorbent article, but will instead be absorbed by the second storage layer 306, which in the plane of the article has a longer extension than the acquisition layer 304 or the first storage layer 305. The acquisition layer 304 is arranged between the first storage layer 305 and the second storage layer 306. The acquisition layer 304 comprises three separate strips extending in the longitudinal direction of the article. Between the strips, there is a space being free from the acquisition material, i.e., the hollow space, 314. Preferably, the strips in the acquisition layer 304 are comprised of a super absorbent foam material, which in a dry condition is highly compressed. Upon wetting such a super absorbent expands heavily in all directions of the material. The hollow spaces 314 render space for the super absorbent foam material to expand without changing the shape of the absorbent structure.

The absorbent structure 303 further comprises a tissue or a substantially hydrophobic nonwoven layer 315, which is arranged between the acquisition layer 304 and the first storage layer 305. The liquid permeable topsheet 301 and the tissue or nonwoven layer 315 are joined to each other. Contact between the layers is obtained in the hollow spaces created in the first storage layer 305 when the apertures/recesses were made. Preferably, it is a thermal joining, but it is also possible to join the liquid permeable top sheet 301 and the tissue or nonwoven layer 315 using an adhesive.

The discharged bodily fluids, for example urine, penetrate through the liquid permeable top sheet 301 and are then brought through the tissue or nonwoven layer 315, whereby they will be rapidly absorbed by the acquisition layer 304. Thereafter, the first storage layer 305 drains the fluids from the acquisition layer 304, whereby the acquisition layer 304 thereafter is prepared to receive the next dose of liquid. The first storage layer 305 has the capacity to store several doses of liquid. In the thickness direction of the first storage layer 305, the walls 316 of the hollow spaces comprise a capillary structure, which is created when the apertures/recesses were made.

Figure 4:
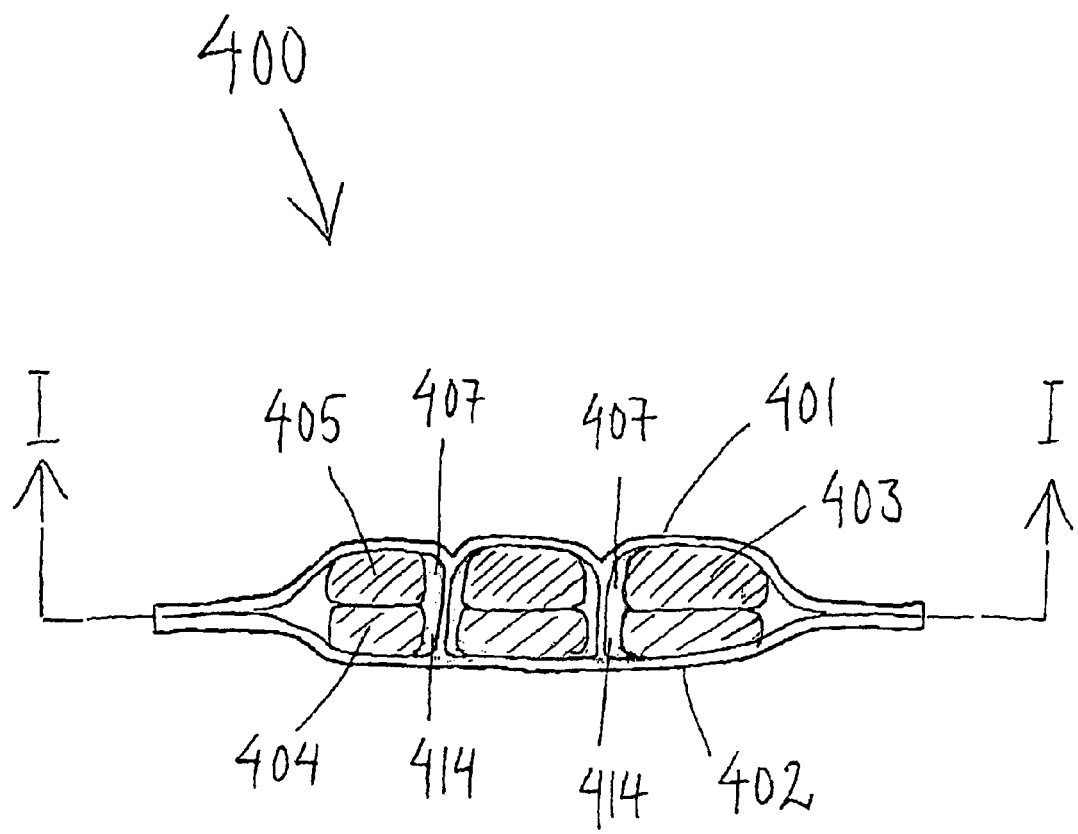
FIG. 4 shows a cross-section of an alternative embodiment of an absorbent article according to the invention.

FIG. 4 shows a cross-section along a transversally extending center line I of an alternative embodiment of an absorbent article 400 according to the invention. The absorbent article 400 has a liquid permeable top sheet 401, which during use of the article 400 is intended to lie closest to the user, a substantially liquid impermeable back sheet 402, and an absorbent structure 403 enclosed therebetween. The absorbent structure 403 comprises an acquisition layer 404, which is intended to be able to rapidly receive a large amount of liquid, and a first storage layer 405, which is intended to be able to rapidly store a large amount of liquid. The storage layer 405 is arranged closest to the liquid permeable top sheet 401 and the acquisition layer 404 is arranged closest to the back sheet 402. The first storage layer 405 has two longitudinally arranged apertures/recesses 407. The first storage layer 405 is a fiber structure containing at least 50 percent by weight of super absorbent material calculated on the total weight of the first storage layer 405. The acquisition layer 404 is constituted of three separate strips of material extending in the longitudinal direction of the article. Between the strips, there is a space being free from the acquisition material, i.e., the hollow spaces, 414. Preferably, the strips in the acquisition layer 404 are comprised of a super absorbent foam material, for example, a polyacrylate-based foam material. A polyacrylate-based foam material is produced by the saturation under pressure using carbon dioxide of a solution, which at least contains monomer, a cross-linking material, an initiator and a tenside in a vessel during stirring. When the solution is removed from the vessel through a nozzle, the solution is expanded and a foamed structure is achieved. The foamed structure is then locked in that polymerisation and cross-linking are initiated by for instance UV radiation and/or e-beam radiation. Finally, the material is compressed and dried.

Upon wetting, such a super absorbent expands heavily in all directions of the material. The hollow spaces 414 provide space for the super absorbent foam material to expand without changing the shape of the absorbent structure 403. The liquid permeable topsheet 401 and the back sheet 402 are joined to each other. Contact between the layers 401, 402 is obtained in the hollow spaces created in the storage layer 405 when the apertures/recesses were made. Preferably, it is a thermal joining, but it is also possible to join both layers using an adhesive.

EXAMPLE 1

The liquid absorption capacity of the storage layer has been measured for two separate cases. In the first case, liquid is applied to the upper surface of a storage layer not exhibiting any apertures/recesses (sample 1). In the second case, liquid has been applied to the upper surface of a storage layer, which has been cut in the longitudinal direction, in a way that it would constitute a number of separate strips, whereby the strips have been placed with a distance of 1 millimeter from each other (sample 2).

The samples were a mixed structure containing cellulosic fibers and super absorbent particles. The cellulosic fibers were provided from Weyerhauser and are denoted NB 416.

The super absorbent material was a particulate polyacrylate-based super absorbent material from BASF. The super absorbent material is denoted 7160. The samples contained 60 percent by weight of the super absorbent material based on the total weight of the samples.

The area of the test samples was 19.6 $cm^2$. The measurements were performed by putting the samples in a petri dish and subsequently adding 10 ml of a sodium chloride solution to the upward facing surface of the sample in the petri dish. The concentration of sodium chloride was 0.9 grams NaCl per liter water. Thereafter, the time for the samples to absorb the liquid was measured. "Total density" refers to the density of the whole structure, i.e., the mixed structure containing super absorbent material and cellulosic fibers.

TABLE 1

| Sample | Total density (g/$cm^3$) | Absorption rate (sec.) |
|---|---|---|
| Sample 1 | 0.33 | 9 |
| Sample 2 | 0.33 | 8 |
| Sample 1 | 0.45 | 14 |
| Sample 2 | 0.45 | 8 |

The results show that at a high density, it is especially advantageous having apertures/recesses in the material.

EXAMPLE 2

The stiffness of the acquisition layer has been measured. The equipment used for the measurement is the "Gurley Precision Instruments Troy" made in New York, USA. The measurements were performed according to the method description "Instructions for Gurley bending resistance/stiffness testers, models 4171 C, D, E". During the measurements, the digital method 4171-D was used.

Tested Materials

Sample 3 is a mixed structure of chemically manufactured cellulosic fluff pulp from Weyerhauser and a particulate polyacrylate-based super absorbent material from BASF. The mixed structure contains 40 percent by weight super absorbent material based on the total weight of the sample.

Sample 4 is a fiber structure from Weyerhauser. The fiber structure contains 80 percent by weight cross-linked cellulose and 20 percent by weight thermoplastic fibers.

Sample 5 is a polyester fiber layer having particulate polyacrylate-based super absorbent material bound to the polyester fiber layer. The percentage of super absorbent particles is 60 percent based on the total weight of the sample.

Sample 6 is a polyacrylate-based super absorbent foam layer. The foam layer is denoted Foam XII and is described in more detail in Example 3.

Sample 7 is a polyacrylate-based super absorbent foam layer. The foam layer is denoted Foam XV and is described in more detail in Example 3.

Sample 8 is a viscose foam material, i.e., a foam material from regenerated cellulose.

The measurements were performed at three different densities for all samples. The samples were measured at the densities 0.50 g/$cm^3$, 0.71 g/$cm^3$, and 0.91 g/$cm^3$. The samples were compressed to the given density and after 10-30 seconds, the samples were placed in the test equipment. In the table below the results from the measurements are shown. The density is given in g/$cm^3$ and the stiffness in milligrams.

TABLE 2

| | Gurley stiffness (milligrams) | | |
|---|---|---|---|
| Sample | 0.50 g/$cm^3$ | 0.71 g/$cm^3$ | 0.91 g/$cm^3$ |
| Sample 3 | 1343 | 2364 | 2359 |
| Sample 4 | 3437 | 3623 | 3823 |
| Sample 5 | 5090 | 5894 | 6088 |
| Sample 6 | 105 | 69 | 56 |
| Sample 7 | 274 | 123 | 141 |
| Sample 8 | 9246 | 5690 | 5023 |

The results clearly show that the super absorbent foam layers, i.e., sample 6 and sample 7, are significantly softer and more flexible than the other test samples.

EXAMPLE 3

The pores in the acquisition layer made of polyacrylate-based foam materials have been characterised by means of a Liquid Porosimeter equipment from Textile Research Institute, Princeton, USA. The function of the equipment is described in detail in Miller, B. and Tyomkin, I. in Journal of Colloid and Interface Science, 162, 163-170 (1994).

The tested materials are two kinds of polyacrylate-based foam materials, Foam XII and Foam XV, respectively. Foam XII has been made according to the following:

To a beaker the following is added:

348.5 grams of acrylic acid (4.84 moles)

135.5 grams of a sodium acrylate solution containing 37.3 percent per weight (0.54 moles)

28.0 grams of polyethylene glycol diacrylate from polyethylene glycol having a molecular weight of 400.

21.3 grams of a aqueous solution 15 percent per weight containing ethylene oxide and linear $C_{16}$-$C_{18}$ fatty alcohol (molar ratio 80:1) 65.7 grams of water.

The ingredients were mixed and thereafter, the solution was cooled to a temperature lower than 16 (C). The solution was the poured into a closed container, whereby the solution was saturated with carbon dioxide at a pressure of 12 bars for 25 minutes. Using the same pressure, 26.7 grams of an aqueous solution containing 3 percent by weight of 2,2'-azobis(2-amidinopropane) dihydrochloride was added. This was mixed to a homogenous solution. The solution was then allowed to rest for five minutes. The saturated solution was discharged from a container using a nozzle having an opening being 1 mm at a pressure of 12 bars. The resulting monomeric foam was placed on a glass plate (DIN-A3). An additional glass plate was then placed on top of the monomeric foam. Then, the foam was polymerized using a UV/NIS lamp, a UV1000 lamp from Hbhnle. The foam was illuminated using the lamp both from underneath and from above. The illumination and thereby also the polymerization were allowed to proceed for 4 minutes. Foam XV was made in the same way. The difference between Foam XII and Foam XV was that more cross-linking agent (i.e., polyethylene glycol diacrylate) was used for making Foam XV. 40.0 grams of polyethylene glycol diacrylate instead of 28.0 grams were added for making Foam XV.

$PV_{50}$ is the pressure when 50% of the drainable pores have been emptied. The super absorbent foam materials that are shown to be especially advantageous, exhibit a $PV_{50}$ value lower than 12 cm $H_2O$. The $PV_{50}$ value is obtained by measuring the amount of liquid as a function of the pressure in the chamber in a receding measurement and register when 50% of the drainable pores have been emptied. Upon a receding measurement, the amount of liquid is measured, being emptied from a porous material at a certain pressure in the chamber. At the measurement excess liquid is delivered to the sample. The sample is allowed to absorb this liquid. Then the sample is placed in the chamber on a membrane and a porous plate. A mechanical load is applied. Thereafter the chamber is closed and the air pressure inside the chamber is raised successively in steps by means of a computer-controlled pressure maintaining system, whereby the liquid leaves the sample through a membrane having small pores. The weight of the squeezed liquid is registered using a beam balance.

The amount of liquid present in the sample upon full saturation when it is in the chamber is estimated, $M_o(g)$. The liquid remaining in the sample when the pressure in the chamber exceeds 50 cm $H_2O$ is considered to be a difficultly drainable liquid. This amount of liquid is estimated $M_D(g)$. The pressure at which 50% of the drainable liquid has been drained out of the samples is calculated according to the following:

$$M_{50\%} = 0.5(M_o - M_D) + M_D$$

From the protocol from receding measurements, the pressure at which the chamber had when the sample contained the amount $M_{50\%}$, can be estimated. This pressure is the $PV_{50}$ value. $PV_{50}$ should be lower than 12 cm $H_2O$, more preferably lower than 8 cm $H_2O$, and most preferably lower than 6 cm $H_2O$. For the material to be able to keep the liquid in a satisfactory manner, the $PV_{50}$ value should not be lower than 2 cm $H_2O$, and preferably not lower than 4 cm $H_2O$.

A more detailed description of how the measurements were performed follows below.

Before the measurement the samples were kept in sealed plastic bags in order to avoid absorption of moisture from the air. The dry sample was weighed. Thereafter, the sample was placed in the test chamber on membranes (Millipore 0.22 μm cat. No. GSWP 09000), whereby the sample was allowed to swell in excess liquid during 30 minutes. The size of the sample after swelling was 10-25 $cm^2$.

For this measurement synthetic urine was used. The ion concentration in the liquid was 0.135 M sodium, 0.086 M potassium, 0.0035 M magnesium, 0.002 M calcium, 0.19 M chloride, 0.0055 M sulphate, and 0.031 phosphate. Additionally, the liquid contained 0.3 M urea and 1 ppm w/w Triton TX-100 (Calbiochem-648462). The liquid was made in such a way that no salts were precipitated.

A load covering the whole sample surface was placed on the sample during the swelling and the measurement. To avoid measuring pores between the sample surface and the load and to maintain an equal load distribution over the whole sample surface, non-absorbent polyurethane foam was placed between the sample and the applied load. The total load put on the swelled sample was 0.3 kPa.

The equilibrium velocity, i.e., the velocity when the weight change at the selected air pressure had decreased to an insignificant level, was upon measuring 5 mg/min and the measure time during which the weight change was recorded was 30 seconds. The measurements were made at the following applied air pressures measured in cm $H_2O$: 1.1, 1.2, 1.4, 1.7, 2.0, 2.2, 2.4, 2.7, 3.1, 3.5, 4.1, 4.4, 4.7, 5.1, 5.6, 6.1, 6.8, 7.7, 8.7, 10.2, 11.1, 12.2, 13.6, 15.3, 17.5, 20.4, 24.5, 30.6, 40.8, 49.0, 61.2.

To record the remaining liquid, the sample was weighed directly after each terminated measurement. In addition to the measurement of samples, one blank control run was performed. For the control run, only foam and load was placed in the test chamber. The measurement was performed the same way and using the same conditions as for the sample measurements. The control run is then subtracted from the sample run before continued processing of raw data.

TABLE 3

| Sample | $PV_{50}$ |
| --- | --- |
| Foam XII | 5.3 cm $H_2O$ |
| Foam XV | 17 cm $H_2O$ |

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. An absorbent article comprising a longitudinal direction, a transverse direction, a liquid permeable upper surface, a liquid impermeable lower surface, and an absorbent structure arranged between the liquid permeable upper surface and the liquid impermeable lower surface, which article in the longitudinal direction has a crotch portion and two end portions, wherein the absorbent structure comprises an acquisition layer and at least one first storage layer, wherein said first storage layer comprises at least 50 percent by weight of a super absorbent material calculated on the total weight of the first storage layer, wherein the first storage layer in a dry condition has a density exceeding 0.4 g/cm$^3$, and said first storage layer in the crotch portion of the absorbent structure has at least one longitudinally extending aperture having a longitudinal dimension in the longitudinal direction of the article that is greater than a transverse dimension in the transverse direction of the article, the aperture extending through an entire thickness of the first storage layer, wherein the first storage layer has a first surface facing the liquid permeable upper surface of the article, and a second surface facing away from the liquid permeable surface of the article, wherein the first storage layer lies between the acquisition layer and the liquid permeable upper surface.

2. The absorbent article according to claim 1, wherein the first storage layer has a density exceeding 0.5 g/cm$^3$.

3. The absorbent article according to claim 1, wherein the first storage layer comprises at least 70 percent by weight of a super absorbent material calculated on the total weight of the first storage layer.

4. The absorbent article according to claim 1, wherein the at least one aperture comprises a longitudinal channel.

5. The absorbent article according to claim 1, wherein material between the apertures, in the crotch portion of the first storage layer, exhibits a width being maximally 20 mm.

6. The absorbent article according to claim 1, wherein the absorbent article comprises a liquid permeable top sheet, wherein the liquid permeable top sheet and the acquisition layer are thermally joined in a hollow space in the first storage layer created by said apertures.

7. An absorbent article comprising a liquid permeable upper surface, a liquid impermeable lower surface, and an absorbent structure arranged between the liquid permeable upper surface and the liquid impermeable lower surface, which article in the longitudinal direction has a crotch portion and two end portions, wherein the absorbent structure comprises an acquisition layer and at least one first storage layer, wherein said first storage layer comprises at least 50 percent by weight of a super absorbent material calculated on the total weight of the first storage layer, wherein the first storage layer in a dry condition has a density exceeding 0.4 g/cm$^3$, and said first storage layer in the crotch portion of the absorbent structure has longitudinally extending apertures extending through an entire thickness of the first storage layer, wherein the first storage layer has a first surface facing the liquid permeable upper surface of the article, and a second surface facing away from the liquid permeable surface of the article, wherein the first storage layer lies between the acquisition layer and the liquid permeable upper surface, and wherein the acquisition layer is a super absorbent foam material.

8. An absorbent article comprising a liquid permeable upper surface, a liquid impermeable lower surface, and an absorbent structure arranged between the liquid permeable upper surface and the liquid impermeable lower surface, which article in the longitudinal direction has a crotch portion and two end portions, wherein the absorbent structure comprises an acquisition layer and at least one first storage layer, wherein said first storage layer comprises at least 50 percent by weight of a super absorbent material calculated on the total weight of the first storage layer, wherein the first storage layer in a dry condition has a density exceeding 0.4 g/cm$^3$, and said first storage layer in the crotch portion of the absorbent structure has longitudinally extending apertures extending through an entire thickness of the first storage layer, wherein the first storage layer has a first surface facing the liquid permeable upper surface of the article, and a second surface facing away from the liquid permeable surface of the article, wherein the first storage layer lies between the acquisition layer and the liquid permeable upper surface, the acquisition layer is a polyacrylate based super absorbent foam material, and said foam material exhibits a Gurley stiffness value lower than 1000 mg and a density in a dry condition exceeding 0.5 g/cm$^3$.

9. An absorbent article comprising a liquid permeable upper surface, a liquid impermeable lower surface, and an absorbent structure arranged between the liquid permeable upper surface and the liquid impermeable lower surface, which article in the longitudinal direction has a crotch portion and two end portions, wherein the absorbent structure comprises an acquisition layer and at least one first storage layer, wherein said first storage layer comprises at least 50 percent by weight of a super absorbent material calculated on the total weight of the first storage layer, wherein the first storage layer in a dry condition has a density exceeding 0.4 g/cm$^3$, and said first storage layer in the crotch portion of the absorbent structure has longitudinally extending apertures extending through an entire thickness of the first storage layer, wherein the first storage layer has a first surface facing the liquid permeable upper surface of the article, and a second surface facing away from the liquid permeable surface of the article, wherein the first storage layer lies between the acquisition layer and the liquid permeable upper surface, and wherein the acquisition layer is a fibrous layer including polyacrylate-based particles or a polyacrylate-based coating bonded to the fibrous layer, wherein the polyacrylate-based particles or the polyacrylate-based coating is bonded to the fibrous layer by spraying acrylic acid monomers onto the fibrous layer whereby the acrylic acid monomer is allowed to polymerise.

10. The absorbent article according to claim 1, wherein the acquisition layer is corona treated.

11. The absorbent article according to claim 1, wherein the absorbent structure further comprises a second storage layer containing a lower amount of super absorbent material calculated on the total weight of the storage layer than the first storage layer, the second storage layer being arranged between the acquisition layer and the liquid impermeable lower surface.

12. An absorbent article comprising a liquid permeable upper surface, a liquid impermeable lower surface, and an absorbent structure arranged between the liquid permeable upper surface and the liquid impermeable lower surface, which article in the longitudinal direction has a crotch portion and two end portions, wherein the absorbent structure comprises an acquisition layer and at least one first storage layer, wherein said first storage layer comprises at least 50 percent by weight of a super absorbent material calculated on the total weight of the first storage layer, wherein the first storage layer in a dry condition has a density exceeding 0.4 g/cm$^3$, and said first storage layer in the crotch portion of the absorbent structure has longitudinally extending apertures extending through an entire thickness of the first storage layer, wherein the first storage layer has a first surface facing the liquid permeable upper surface of the article, and a second surface facing away from the liquid permeable surface of the article, wherein the first storage layer lies between the acquisition layer and the liquid permeable upper surface, and wherein the absorbent structure further comprises a second storage layer and wherein the second storage layer partly or entirely encloses the first storage layer, the second storage layer being arranged between the acquisition layer and the liquid impermeable lower surface.

13. An absorbent article comprising a longitudinal direction, a transverse direction, a liquid permeable upper surface, a liquid impermeable lower surface, and an absorbent structure arranged between the liquid permeable upper surface and the liquid impermeable lower surface, which article in the longitudinal direction has a crotch portion and two end portions, wherein the absorbent structure comprises an acquisition layer and at least one first storage layer comprising a super absorbent material, the first storage layer having a greater ability to retain liquid than the acquisition layer, and being located between the acquisition layer and liquid permeable upper surface and said first storage layer in the crotch portion of the absorbent structure has at least one longitudinally extending aperture having a longitudinal dimension in the longitudinal direction of the article that is greater than a transverse dimension in the transverse direction of the article, the aperture extending through an entire thickness of the first storage layer, wherein the first storage layer has a first surface facing the liquid permeable upper surface of the article, and a second surface facing away from the liquid permeable surface of the article.

14. The absorbent article according to claim 13, wherein the first storage layer comprises at least 50 percent by weight of a super absorbent material calculated on the total weight of the first storage layer.

15. The absorbent article according to claim 13, wherein the first storage layer in a dry condition has a density exceeding $0.4 \text{ g/cm}^3$.

16. The absorbent article according to claim 13, wherein the absorbent structure further comprises a second storage layer containing a lower amount of super absorbent material calculated on the total weight of the storage layer than the first storage layer, the second storage layer being arranged between the acquisition layer and the liquid impermeable lower surface.

17. An absorbent article comprising a liquid permeable upper surface, a liquid impermeable lower surface, and an absorbent structure arranged between the liquid permeable upper surface and the liquid impermeable lower surface, which article in the longitudinal direction has a crotch portion and two end portions, wherein the absorbent structure comprises an acquisition layer and at least one first storage layer comprising a super absorbent material, the first storage layer having a greater ability to retain liquid than the acquisition layer, and being located between the acquisition layer and liquid permeable upper surface and said first storage layer in the crotch portion of the absorbent structure has longitudinally extending apertures extending through an entire thickness of the first storage layer, wherein the first storage layer has a first surface facing the liquid permeable upper surface of the article, and a second surface facing away from the liquid permeable surface of the article, and wherein the absorbent structure further comprises a second storage layer and wherein the second storage layer partly or entirely encloses the first storage layer, the second storage layer being arranged between the acquisition layer and the liquid impermeable lower surface.

18. The absorbent article according to claim 1, wherein the at least one aperture is in the form of a longitudinal channel adapted to direct liquid in a direction towards the end portions of the absorbent structure.

19. The absorbent article according to claim 1, wherein the at least one aperture is a space capable of holding liquid before the liquid is absorbed by the first storage layer.

20. The absorbent article according to claim 13, wherein the at least one aperture is in the form of a longitudinal channel adapted to direct liquid in a direction towards the end portions of the absorbent structure.

21. The absorbent article according to claim 13, wherein the at least one aperture is a space capable of holding liquid before the liquid is absorbed by the first storage layer.

22. The absorbent article according to claim 7, wherein the super absorbent foam material is polyacrylate based.

23. The absorbent article according to claim 13, wherein the acquisition layer is a super absorbent foam material.

24. The absorbent article according to claim 23, wherein the super absorbent foam material is polyacrylate based.

25. The absorbent article according to claim 13, wherein the acquisition layer is a fibrous layer including polyacrylate-based particles or a polyacrylate-based coating bonded to the fibrous layer, wherein the polyacrylate-based particles or the polyacrylate-based coating is bonded to the fibrous layer by spraying acrylic acid monomers onto the fibrous layer whereby the acrylic acid monomer is allowed to polymerise.

26. The absorbent article according to claim 1, wherein the first storage layer directly contacts a topsheet defining the liquid permeable upper surface, and the at least one longitudinally extending aperture is empty.

27. The absorbent article according to claim 13, wherein the first storage layer directly contacts a topsheet defining the liquid permeable upper surface, and the at least one longitudinally extending aperture is empty.

* * * * *